United States Patent [19]

Bola

[11] Patent Number: 5,489,439
[45] Date of Patent: Feb. 6, 1996

[54] GRANULAR PHARMACEUTICAL FORMULATIONS

[75] Inventor: Tarlok S. Bola, Ilford, England

[73] Assignee: May & Baker Ltd., Essex, England

[21] Appl. No.: 203,471

[22] Filed: Oct. 19, 1993

Related U.S. Application Data

[63] Continuation of Ser. No. 13,487, Feb. 1, 1993, abandoned, which is a continuation of Ser. No. 895,162, Jun. 5, 1992, abandoned, which is a continuation of Ser. No. 414,259, Sep. 29, 1989, abandoned.

[30] Foreign Application Priority Data

Sep. 30, 1988 [GB] United Kingdom ............ 8823082
Apr. 5, 1989 [GB] United Kingdom ............ 8907658

[51] Int. Cl.⁶ ................................................. A61K 9/14
[52] U.S. Cl. ................... 424/489; 424/458; 424/490
[58] Field of Search .................. 424/489, 490, 424/491, 488

[56] References Cited

U.S. PATENT DOCUMENTS

| 2,793,979 | 5/1957 | Svedres | 424/470 |
| 4,066,756 | 1/1978 | Orr | 514/161 |
| 4,743,247 | 5/1988 | Wong | 424/468 |
| 4,777,033 | 10/1988 | Ikura | 424/488 |

FOREIGN PATENT DOCUMENTS

| 385654 | 4/1984 | Austria. |
| 0094116 | 4/1983 | European Pat. Off.. |
| 94116 | 1/1984 | European Pat. Off.. |
| 0192321 | 1/1986 | European Pat. Off.. |
| 192321 | 1/1986 | European Pat. Off.. |
| 2028224 | 10/1969 | Germany. |

OTHER PUBLICATIONS

Journal of Pharmacy and Pharmacology, vol. 36, Sep. 1984, London W. J. Thiel et al. "Fluidized bed film coating of an ordered powder mixture to produce microencapsulated ordered units" pp. 145–152.

Die Pharmazie, 34, vol. 12, Dec. 1979, Berlin H. Kala et al. "Anwedung der spruhtrocknug in der Pharmazie" pp. 779–784.

Schmidt and Benke, "Drugs made in Germany", (1985), vol. 28, pp. 49–55.

J. Pharm. Pharmacol., 1986, 38, 166–171.

J. Pharm. Pharmacol, 1987, 39, 329–334.

European Search Report, dated Dec. 22, 1989.

*Primary Examiner*—Thurman K. Page
*Assistant Examiner*—William E. Benston, Jr.
*Attorney, Agent, or Firm*—Finnegan, Henderson, Farabow, Garrett & Dunner

[57] ABSTRACT

A process for the preparation of a granule comprising a pharmaceutical which process comprises contacting a particulate, spray-dried substrate and a particulate pharmaceutical to obtain a particle comprising a substrate core carrying an adsorbed pharmaceutical and contacting the particle with a particulate pharmaceutical and a melted or thermally softened pharmaceutically acceptable excipient which is solid at room temperature to obtain, after cooling to solidify or harden the excipient, a granule comprising a spray-dried substrate core carrying pharmaceutically acceptable excipient and pharmaceutical.

18 Claims, No Drawings

GRANULAR PHARMACEUTICAL FORMULATIONS

This is a continuation of application Ser. No. 08/01.3, 487, filed on Feb. 1, 1993 abandoned, which is a continuation of application Ser. No. 07/895,162, filed on Jun. 5, 1992 abandoned, which is a continuation of application Ser. No. 07/414,259, filed on Sep. 29, 1989 abandoned.

This invention relates to a novel, granular pharmaceutical composition, particularly suitable for use in dispersible formulations, and a process for its production.

Granulation is widely used for the production of pharmaceutical compositions and several basic process types can be distinguished, including dry, wet, and melt or imbedding techniques. A number of other processes can also be used including adsorption onto carriers (an example of which is the adsorption of drugs onto carbohydrates, such as lactose, for use in dry powder aerosols).

More particularly, it is known that certain pharmaceuticals, or combinations thereof, can be adsorbed onto spray dried sorbitols (e.g. Merck "Sorbit-Instant"; P. C. Schmidt & K. Benke "Drugs Made In Germany" (1985) vol. 28 p. 49–55). It is also known that other similar spray-dried materials, such as lactose and dextrose are capable of adsorbing certain substances (W. J. Thiei & L. T. Nguyen, J. Pharm. Pharmacol., 1984, 36, 145–152). The resultant particulate materials are stated to show a high level of physical stability in some instances. This particular adsorption appears to result from electrostatic interaction between adsorbent and adsorbate—potentiated by the open, three-dimensional network structure of the adsorbent.

We have now found that many other pharmaceuticals can also be readily adsorbed onto such substrates. However, in practice only relatively low levels of pharmaceutical can be adsorbed before the carrier is saturated. (In a typical case (that of ketoprofen on sorbitol) this is 7–8% by weight). The pharmaceutical is also relatively exposed and this can be disadvantageous. This exposure can, for example, cause storage stability problems for sensitive pharmaceuticals, allow bitter or irritant pharmaceuticals to affect the oral or gastric mucosa upon ingestion, or result in metabolic inactivation before the pharmaceutical reaches the target site for absorption. In order to reduce this exposure it is often desirable to coat the particles.

Surprisingly, in view of a prior art statement that certain sorbitol-based particles can withstand the stresses imposed on them under air-jet sieving (and would hence apparently be stable to normal handling procedures), it has been found by others that, under stable. Furthermore, we have found that they also do not survive the coating processes used in industry to apply known film coatings (for example enteric soluble, sustained release or taste masking coatings) onto small drug particles. The vigorous agitation resulting from mechanical movement, spray pressure, or extraction air flow in these processes results in considerable breakdown and loss of active agent (which is only present at a relatively low level in any event) of up to 50%. It is also known that other similar spray-dried substrates tend to retain adsorbates less effectively than sorbitol when subjected to similar processing.

Any coating processes which are carried out on such particles also cause agglomeration and clumping, resulting in decreased efficiency and processing difficulties.

As a result of research and experimentation it has been found possible to stabilise adsorbed pharmaceutical on a spray-dried substrate core and also to incorporate additional pharmaceutical by using certain excipients which act as binders.

The invention therefore provides a process for the preparation of granules comprising pharmaceutical, which process comprises contacting a particulate, spray-dried substrate and particulate pharmaceutical to obtain particles comprising a substrate core carrying adsorbed pharmaceutical and contacting those particles with particulate pharmaceutical and a melted or thermally softened pharmaceutically acceptable excipient which is solid at room temperature to obtain, after cooling to solidify or harden the excipient, granules comprising a spray-dried core carrying pharmaceutical and pharmaceutically acceptable excipient.

It will be appreciated that a single pharmaceutical or a combination of pharmaceuticals may be used in any part of this process.

In a preferred embodiment of the invention an excess of particulate pharmaceutical is contacted with the spray-dried substrate to obtain a mixture of particles carrying adsorbed pharmaceutical and excess pharmaceutical, and a solid pharmaceutically acceptable excipient is added to the mixture which is heated to melt or soften the excipient and subsequently cooled to obtain particles carrying pharmaceutically acceptable excipient and pharmaceutical. In this embodiment the excipient is uniformly distributed throughout the mixture before heating which facilitates adherence of the excess pharmaceutical and excipient to the particles which already carry adsorbed pharmaceutical.

The invention also provides granules which comprise a spray-dried substrate core which carries adsorbed pharmaceutical and, it; addition, a layer comprising a pharmaceutically acceptable excipient and pharmaceutical.

The pharmaceutical may be bound to the substrate surface by the excipient either physically (i.e. as individual "glued" particles), in solid solution, or by a combination of both means. The precise mode of retention depends on the properties of the excipient and pharmaceutical used.

Preferred substrates are spray-dried carbohydrates, for example sugars, such as lactose and dextrose, and sugar alcohols, such as sorbitol or mannitol. Spray-dried sorbitol is particularly preferred.

Preferred pharmaceuticals include anti-inflammatories such as ketoprofen [2-(3-benzoylphenyl)propionic acid] and indomethacin [1-(4-chlorobenzoyl)- 5-methoxy-2-methyl-3-carboxymethylindole], bronchodilators such as salbutamol [2-t.butylamino-1-(4-hydroxy-3-hydroxymethylphenyl)e-thanol], anti-allergics/anti-arthritics such as tetrazole- 5-(3-acetyl-5-fluoro-2-hydroxy)carboxanilide [Compound (I)], sedatives such as zopiclone [6-(5-chloropyrid-2-yl)-6,7-dihydro-7- oxo-5H-pyrrolo[3,4-b]pyrazir-5-yl 4-methylpiperazine-1-carboxylate]and β-blockers such as acebutolol [N-{3-acetyl-4-(2-hydroxy-3-[1-methylethyl] aminopropoxy)phenyl butanamide]. These can be used in the form of the compounds themselves or in the form of pharmaceutically acceptable salts (e.g. hydrochlorides of basic materials).

Suitable materials for use as the pharmaceutically acceptable excipient soften or melt between room temperature and the highest temperature at which the initially formed adsorbate/carrier particles are stable, typically 40°–80° C. in the case of sorbitol based substrates. They are also capable of wetting both the initially formed particles carrying adsorbed pharmaceutical and the unadsorbed pharmaceutical whilst in the softened or molten state and preferably do not dissolve the substrate. They can be incorporated by a variety of methods provided that the temperature during at least part of the process is above the softening or melting temperature of the excipient or excipient mixture used.

Preferred excipients are lipids and waxes. Particularly preferred are fatty acids, especially stearic acid; carboxylate esters, especially those of glycerol, glycols and polyglycols (for example Gelucires such as Gelucire 64/02); polyethylene glycols; and mixtures thereof, optionally with other excipients.

Lipids and waxes are well known as binders in a variety of formulations and stearic acid is specifically known as a lubricant in numerous granulating and tabletting processes. The particular usage in the present invention is different from those previously described in that the pharmaceutical and the excipient are jointly adsorbed onto the substrate carrying the initial load of pharmaceutical and form a coherent layer as may be seen from Scanning Electron Microscope photographs of the final products.

Such photographs also show that the pharmaceutical is bound to substrate particles of all sizes. From a practical point of view it is, however, desirable only to use granules of a particular size or size range—normally above a certain minimum size—in final formulations. To facilitate this, it is advantageous to use substrate particles which are substantially larger than those of the pharmaceutical and which are also of approximately the required final size or size range. This also allows the ready removal of any unadsorbed materials or abraded substrate by sieving. Typically, substrate materials having a particle size of 150–1000 μ (e.g. 250–500 μ) and pharmaceutical with a particle size of less than 150 μ (e.g. less than 100μ) are used. Such limits enable the separation of active granules from unwanted fine material by using a sieve, for example of 125 or 150 μ.

The final composition of the granules depends upon a number of factors. For example, the amount of pharmaceutical will depend upon the drug potency and required dosage and upon the intended granule content of any final composition and the amount of excipient will depend upon the surface area and type of substrate and upon the nature of the pharmaceutical and excipient and their mutual interactions. Typical granules comprise 2–25% (w/w) pharmaceutical and up to 25% (w/w) excipient.

The granules may themselves be suitable for use without further processing, as the excipient can itself act as a dissolution retarding or enhancing, and/or taste masking agent, in addition to having an adsorbate stabilising action, and this may be all that is required.

Normally, however, the granules will be subjected to further treatment(s) and they are, for example, stable enough to be further coated to form, for example, enteric or sustained release products via various coating processes including spray or pour methods in apparatus such as granulators, or pan or fluid bed coaters.

The content of pharmaceutical in the coated granules indicates that essentially no loss occurs during the coating process (for example an 18–20% (w/w) active agent level is reduced by addition of the coating weight to 16–17% (w/w) when ketoprofen-containing granules are coated).

Coated and uncoated granules can both be used in the preparation of formulations such as sustained release, pulsed release and enteric products, for example in the form of tablets. They are however especially suitable for making formulations of the above types which are to be administered in the form of suspensions or dispersions.

Individually, both uncoated and coated granules will allow for a wide variability of release rate, depending on the choice of excipient(s) and coating material(s). Mixtures of coated and uncoated, or different types of coated or uncoated, granules will give pulsed, or other release pattern, formulations, as is known in the art.

It is also possible to use, in granules according to the invention, drug or drug-excipient mixtures which would otherwise not be physically or chemically compatible.

Dispersible formulations may contain further excipients including suspending agents such as sodium carboxymethylcellulose, acidulants such as citric acid or adipic acid, sweeteners such as acesulfame-K or aspartame, lemon or other flavourings, colouring agents such as titanium dioxide, and bulking agents such as sugar alcohols (e.g. mannitol or sorbitol)—which may be of the spray-dried type, as well as other conventional excipients.

A typical final composition for a single dose of a dispersible formulation (in the case of coated, ketoprofen-containing granules having an active ingredient content of 15–20% (w/w)) is in the range:

| Granules | 250–667 mg |
| --- | --- |
| Suspending agent | 100–150 mg |
| Acidulant | 50–75 mg |
| Sweetener | 10–30 mg |
| Flavouring | 0–30 mg |
| Colouring | 0–30 mg |
| Bulking agent | q.s. |

Tablets made from granules according to invention may be made by compression of the coated or be made from mixtures containing further conventional excipients, such as disintegrants (e.g. optionally cross-linked sodium carboxymethylcellulose), bulking agents (e.g microcrystalline cellulose) and flow promoters and hardeners (e.g. silica) and may also contain other conventional granulations.

The following Examples illustrate the invention. Unless otherwise indicated all percentages are on a weight for weight basis.

EXAMPLE 1

Preparation of granules

Ketoprofen B. P. (<100 μ; 600 g) and spray-dried sorbitol (Sorbit Instant Merck 3140; 250–500 μ; 1860 g) were mixed using a Hobart mixer under gentle heating for 4 minutes. Stearic acid BPC powder (540 g) was then added and stirring continued for a further 45 minutes during which period the temperature was raised sufficiently to melt the stearic acid. The mixture was allowed to cool under stirring for a further 35 minutes to give an essentially quantitative yield of granular product. Sieving of a sample showed that the 125–800 μ fraction (83.1% of the sample) had an active ingredient content of 18.9%.

EXAMPLE 2

Coating of granules

A spray coating solution was made by dissolving, with vigorous stirring, hydroxypropylmethylcellulose phthalate (Shin Etsu HP50; 640 g) in a mixture of methylene chloride (3680 g) and methanol (3680 g).

400 grams of granules prepared as in Example 1 were placed in a fluidised bed chamber and gently fluidised by means of air containing a small amount of steam as a static eliminator.

500 grams of spray solution were then used to coat the fluidised granules via an atomising nozzle at a temperature of 20°–40° C. Upon completion of spraying the granules were left fluidising for a further 5 minutes and then removed to yield 432 g of coated granules. Sieving of a sample showed that the 150–800 μ fraction (93.0% of the sample) had an active ingredient content of 16.7%.

EXAMPLE 3

Proceeding in a similar manner to that of Example 1, granules were prepared from:

| | |
|---|---|
| Indomethacin B.P. (<100μ) | 25 g |
| Stearic acid BPC | 56.4 g |
| Sorbit Instant (250–500μ) | 175 g |

The fraction above 125 μ accounted for 99.3% of the sample and had an active ingredient content of 8.8%.

EXAMPLE 4

Granules were prepared, using the method of Example 1, from:

| | |
|---|---|
| Salbutamol sulphate B.P. (<100μ) | 6.25 g |
| Stearic acid BPC | 75 g |
| Sorbit Instant (250–500μ) | 231.25 g |

The fraction above 125 μ accounted for 99.7% and had an active ingredient content of 2.0%.

EXAMPLE 5

Granules were prepared, using the method of Example 1, from:

| | |
|---|---|
| Ketoprofen B.P. (<100μ) | 50 g |
| Gelucire 64/02 | 42 g |
| Sorbit Instant (250–500μ) | 150 g |

The fraction above 125 μ was 97.6% and had an active ingredient content of 19.0%.

EXAMPLE 6

A dispersible formulation was prepared as follows. Sorbit Instant (4786 g) and titanium dioxide (206 g) were blended in an Oblicone blender and 4846 g of the resultant mix was further blended in the same device with:

| | |
|---|---|
| Aspartame | 240 g |
| Lemon-Juice Flav-O-Lok (flavouring) | 80 g |
| Citric acid | 800 g |
| Sodium carboxymethylcellulose | 1200 g |
| Coated granules (prepared as in Example 2) | 4834 g |

The resultant formulation was filled into sachets each containing 100 mg (nominal) of ketoprofen. (Total fill weight ca. 1.5 g).

EXAMPLE 7

Proceeding in a similar manner to that of Example 6, there was prepared a dispersible formulation consisting of:

| | |
|---|---|
| Coated, ketoprofen-containing granules (17.4% active content) | 38.3% |
| Mannitol | 43.3% |
| Sodium carboxymethylcellulose | 10.0% |
| Adipic acid | 5.0% |
| Titanium dioxide | 1.7% |
| Aspartame | 1.0% |

| | |
|---|---|
| Flavouring | 0.7% |

EXAMPLES 8 to 11

Proceeding in a similar manner to that of Example 1, the following granules were prepared and analysed:

| Example | Active ingredient | Weight | Excipient | Weight |
|---|---|---|---|---|
| 8 | Ketoprofen | 75 g | Polyethylene glycol 6000 | 45 g |
| 9 | Compound (I) | 30 g | Polyethylene glycol 6000 | 45 g |
| 10 | Zopiclone | 5 g | Stearic acid | 20 g |
| 11 | Acebutolol hydrochloride | 10 g | Stearic acid | 20 g |

| Example | Sorbitol weight | Fraction >125μ | Active ingredient of >125μ fraction |
|---|---|---|---|
| 8 | 180 g | 99.9% | 24.9% |
| 9 | 225 g | 98.9% | 9.2% |
| 10 | 75 g | 100.0% | 4.9% |
| 11 | 70 g | 99.9% | 9.4% |

EXAMPLE 12

Uncoated granules, prepared using the method of Example 1, with a ketoprofen content of 20.1%, were compressed using 0.5 inch tooling on a Manesty F3 single punch tabletting machine, to form hard tablets weighing 250–500 mg, with a waxy matrix type structure.

EXAMPLE 13

Proceeding in a similar manner to Example 12, tablets were prepared from coated granules, prepared using the method of Example 2. These were very hard smooth tablets of waxy appearance.

EXAMPLE 14

Dispersible 500 mg tablets were prepared, in a similar manner to Example 12, from a mixture of:

| | |
|---|---|
| Coated granules (prepared as in Example 2) | 56% |
| Microcystalline cellulose | 20% |
| Sodium carboxymethylcellulose (Ac-Di-Sol) | 20% |
| Fumed silica (Aerosil 200) | 4% |

They were readily dispersible in water.

I claim:
1. A granule comprising:
   a solid, spray-dried adsorbent non-pharmaceutical core carrying an adsorbed first pharmaceutical; and
   a coating formed on said adsorbent core, said coating having a stabilizing constituent and a second pharmaceutical constituent, said second pharmaceutical constituent being either the same or different from said adsorbed first pharmaceutical.
2. A granule consisting essentially of:
   a solid, spray-dried adsorbent non-pharmaceutical core carrying an adsorbed first pharmaceutical constituent present in an amount from 2 to 25% by weight;

a coating formed on said adsorbent core, said coating having a stabilizing constituent present in an amount of up to 25% by weight and a second pharmaceutical constituent, said second pharmaceutical constituent being either the same or different from said adsorbed first pharmaceutical constituent for:
  a) sustaining release of said adsorbed first pharmaceutical constituent and/or said second pharmaceutical constituent; or
  b) pulsing release of said adsorbed first pharmaceutical constituent and/or said second pharmaceutical constituent; or
  c) forming an enteric product; or
  d) when said adsorbed first pharmaceutical constituent and said second pharmaceutical constituent are different, for administration of drug or drug-excipient mixtures which would otherwise be either physically or chemically incompatible.

3. A granule according to claim 1 in which said stabilizing constituent is a pharmaceutically acceptable excipient.

4. A granule comprising:
  a solid spray-dried adsorbent non-pharmaceutical carbohydrate core;
  a first pharmaceutical constituent adsorbed by said carbohydrate core in an amount from 2 to 25% by weight of said granule; and
  a coating formed on said carbohydrate core, said coating comprising a pharmaceutically acceptable excipient present in an amount of up to 25% by weight of said granule, and a second pharmaceutical constituent; said excipient being a lipid, a wax, a fatty acid, a carboxylate ester, a polyethylene glycol or mixtures thereof; said second pharmaceutical constituent being either the same or different from said adsorbed first pharmaceutical constituent.

5. A granule according to claim 4 in which the carbohydrate core is a sugar or a sugar alcohol.

6. A granule according to claim 5 in which the core is a lactose, dextrose, sorbitol or mannitol.

7. A granule according to claim 1, in which the spray-dried substrate is a carbohydrate.

8. A granule according to claim 7, in which the substrate is a sugar or sugar alcohol.

9. A granule according to claim 8, in which the substrate is lactose, dextrose, sorbitol or mannitol.

10. A granule according to claim 3 in which the excipient has a melting or softening temperature from room temperature to 80° C.

11. A granule according to claim 10 in which the excipient has a melting or softening temperature from room temperature to 40° C.

12. A granule according to claim 3 in which the excipient is a lipid or wax.

13. A granule according to claim 3 in which the excipient is a fatty acid, a carboxylate ester or a polyethylene glycol.

14. A granule according to claim 13, in which the excipient is stearic acid or a carboxylate ester of glycerol, a glycol, or a polyglycol.

15. A granule according to claim 1, in which the first pharmaceutical is ketoprofen, which is 2-(3-benzoylphenyl)propionic acid, indomethacin, which is 1-(4-chlorobenzoyl)- 5-methoxy-2-methyl-3-carboxymethylindole, salbutamol, which is 2-t.butylamino-1-(4-hydroxy-3-hydroxymethylphenyl)ethanol, tetrazole-5-(3-acetyl-5-fluoro-2-hydroxy)carboxanilide, zopiclone, which is 6-(5-chloropyrid-2-yl)-6,7-dihydro-7-oxo-5H-pyrrolo [3,4-b] pyrazin-5-yl-4-methylpiperzaine-1-carboxylate, acebutolol, which is N-(3-acetyl-4-(2-hydroxy-3-[1-methylethyly]aminopropoxy)phenyl]butanamide, or a pharmaceutically acceptable salt thereof.

16. A granule according to claim 1, which comprises from 2 to 25% by weight of pharmaceutical.

17. A granule according to claim 3, which comprises up to 25% by weight of excipient.

18. A granule according to claim 1, which is coated.

* * * * *